US00PP20467P2

(12) United States Plant Patent
Quesada

(10) Patent No.: US PP20,467 P2
(45) Date of Patent: Nov. 10, 2009

(54) ***DRACAENA* PLANT NAMED 'SONG OF COSTA RICA'**

(50) Latin Name: *Dracaena reflexa lam.*
Varietal Denomination: Song of Costa Rica

(75) Inventor: Eliseo Cambronero Quesada, Los Cerritos (CR)

(73) Assignees: A. C. Alderden, Mijdrecht (NL); R. de Leeuw, Mijdrecht (NL)

( * ) Notice: Subject to any disclaimer, the term of this patent is extended or adjusted under 35 U.S.C. 154(b) by 65 days.

(21) Appl. No.: 11/983,687

(22) Filed: Nov. 10, 2007

(51) Int. Cl.
*A01H 5/00* (2006.01)

(52) U.S. Cl. ..... Plt./383

(58) Field of Classification Search ..... Plt./383
See application file for complete search history.

(56) References Cited

OTHER PUBLICATIONS

UPOV-ROM GTITM, Plant Variety Database, 2008/05, GTI Jouve Retrieval Software, Citation for plant 'Song of Costa Rica'.*

* cited by examiner

*Primary Examiner*—Annette H. Para
*Assistant Examiner*—Susan B McCormick Ewoldt
(74) *Attorney, Agent, or Firm*—Mark P. Bourgeois

(57) ABSTRACT

A new cultivar of *Dracaena* plant named 'Song of Costa Rica' that is characterized by small yellow and light green leaves with dark green margins, a compact habit, short internodes and strong stems.

1 Drawing Sheet

Botanical classification: *Dracaena reflexa* lam.
Variety denomination: 'Song of Costa Rica'

BACKGROUND OF THE INVENTION

The present invention relates to a new and distinct cultivar of *Dracaena* plant botanically known as *Dracaena reflexa* lam. and hereinafter referred to by the cultivar name 'Song of Costa Rica'.

The new cultivar was discovered in 2001 in an outdoor nursery in a cultivated area of Rio Quarto, Costa Rica. 'SONG OF COSTA RICA' was discovered as a naturally occurring branch mutation of *Dracaena reflexa* lam. 'Song of Jamaica' (not patented).

Asexual reproduction by terminal cuttings of the new cultivar 'Song of Costa Rica' was first taken in 2001 in Rio Quarto, Costa Rica.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dracaena* cultivar 'Song of Costa Rica'. These traits in combination distinguish 'Song of Costa Rica' as a new and distinct cultivar.

1. *Dracaena* 'Song of Costa Rica' exhibits small yellow and light green leaves with dark green margins.
2. *Dracaena* 'Song of Costa Rica' exhibits a compact habit.
3. *Dracaena* 'Song of Costa Rica' exhibits short iinternodes.
4. Dracaena 'Song of Costa Rica' exhibits strong stems.

The closest comparison cultivar is the parent plant 'Song of Jamaica'. 'Song of Costa Rica' is distinguishable from 'Song of Jamaica' by the following characteristics:

1. 'Song of Costa Rica' has smaller leaves.
2. 'Song of Costa Rica' has shorter internodes.
3. 'Song of Costa Rica' has stronger stems.

'Song of Costa Rica' is distinguishable from typical plants of the species *Dracaena reflexa* lam. by the following characteristics:

1. 'Song of Costa Rica' has smaller leaves.
2. 'Song of Costa Rica' has shorter internodes.
3. 'Song of Costa Rica' has stronger stems.

BRIEF DESCRIPTION OF THE DRAWING

The accompanying photograph illustrates the distinguishing traits of *Dracaena* 'Song of Costa Rica'.

The plant in the photograph shows an overall view of a 7 month old plant.

The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Dracaena* cultivar named 'Song of Costa Rica'. Data was collected in Boskoop, The Netherlands from plants grown in Honselersdijk, The Netherlands. The time of year was winter. The plants were 7 month old greenhouse grown plants in 15 cm diameter containers. The temperature ranged from 24 to 34° Centigrade. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Song of Costa Rica' has not been tested under all possible conditions and phenotypic differences may be observed with variations in environmental, climatic, and cultural conditions, however, without any variance in genotype.

Botanical classification: *Dracaena reflexa* lam. 'Song of Costa Rica'.

Parentage: 'Song of Costa Rica' was discovered as a naturally occurring branch mutation of *Dracaena reflexa* lam. 'Song of Jamaica'.

Annual or Perennial: Perennial.

Use: Ornamental.

Vigor: Moderate.

Growth habit: Upright.

Plant shape: Columnar.

Suitable container size: 15 cm. container.

Height: Average 71.6 cm. in height.

Width: Average 32.1 cm. in width.

Heat tolerance: Tolerant to 40 degrees Centigrade.

Winter hardiness: USDA Zone 10.

Growth rate: Approximately 4 cm. per month.

Propagation: Terminal cuttings.

Time to initiate roots in summer: Approximately 21 days to produce roots on an initial cutting.

Time to initiate roots in winter: Approximately 23 days to produce roots on an initial cutting.

Time to produce a rooted cutting or liner in summer: Approximately 30 days.

Time to produce a rooted cutting or liner in winter: Approximately 35 days.

Crop Time: Approximately 7 months to produce a finished plant from a rooted cutting.

Root system: Fine and fibrous.

Stem:

*Stem strength.*—Very strong.

*Stem color.*—136B and 137A; older stem 199D.

*Stem pubescence.*—Absent.

*Internode length.*—Average 1.0 cm.

*Stem shape.*—Round.

*Stem surface.*—Smooth.

Foliage:

*Texture.*—Smooth, glossy, slightly leathery.

*Leaf arrangement.*—Alternate.

*Compound or single.*—Single.

*Quantity of leaves.*—Average 67.

*Leaf shape.*—Lorate.

*Leaf apex.*—Apiculate.

*Leaf base.*—Sheathing.

*Leaf length.*—Average 17.9 cm. in length.

*Leaf width.*—Average 2.3 cm. in width.

*Pubescence.*—Absent.

*Leaf margin.*—Entire.

*Vein pattern.*—Parallel.

*Young leaf color* (*upper surface*).—143A with stripes 144B to 144C, margins 143A.

*Young leaf color* (*lower surface*).—Striped 143B and 144B to 144C, margins 138A.

*Mature leaf color* (*upper surface*).—Striped in between 139A and 147A and 144A, margins 139A and 147A.

*Mature leaf color* (*lower surface*).—Center 144A, margins 147A.

*Vein color.*—As leaf blade.

*Leaf attachment.*—Sessile.

*Durability of foliage to stress.*—High.

Flower: Flowering has not been observed.

Disease and pest resistance: 'Song of Costa Rica' has not been observed for disease or pest resistance.

What is claimed is:

1. A new and distinct variety of *Dracaena* plant named 'Song of Costa Rica' as described and illustrated.

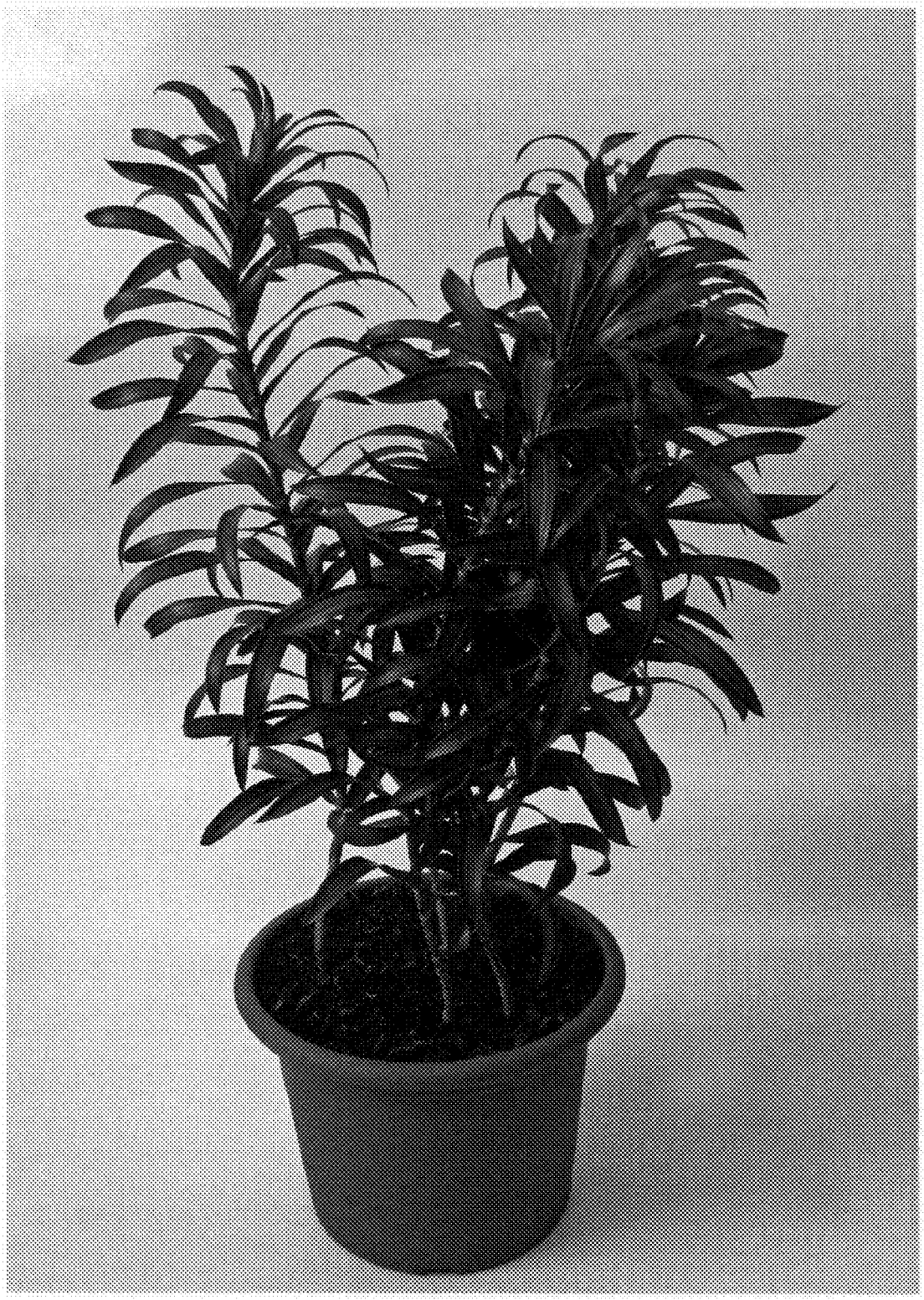

* * * * *